(12) United States Patent
Obrist et al.

(10) Patent No.: US 11,498,094 B2
(45) Date of Patent: Nov. 15, 2022

(54) METHOD OF MAKING A TWO-COMPONENT PISTON

(71) Applicant: Sulzer Mixpac AG, Haag (CH)

(72) Inventors: Manfred Obrist, Lustenau (AT); Philipp Seiler, Au (CH); Renato Brunner, Dornbirn (AT)

(73) Assignee: MEDMIX SWITZERLAND AG, Haag (CH)

( * ) Notice: Subject to any disclaimer, the term of this patent is extended or adjusted under 35 U.S.C. 154(b) by 82 days.

(21) Appl. No.: 16/772,911

(22) PCT Filed: Dec. 14, 2018

(86) PCT No.: PCT/EP2018/084963
§ 371 (c)(1),
(2) Date: Jun. 15, 2020

(87) PCT Pub. No.: WO2019/121398
PCT Pub. Date: Jun. 27, 2019

(65) Prior Publication Data
US 2020/0324313 A1    Oct. 15, 2020

(30) Foreign Application Priority Data
Dec. 20, 2017 (EP) ..................... 17209077

(51) Int. Cl.
*B29C 45/16* (2006.01)
*B05C 17/005* (2006.01)
(Continued)

(52) U.S. Cl.
CPC .. *B05C 17/00579* (2013.01); *B05C 17/00559* (2013.01); *B29C 45/0025* (2013.01);
(Continued)

(58) Field of Classification Search
CPC .......... B29C 45/1676; B29C 2045/167; B29C 2045/1678; B29C 37/0082
See application file for complete search history.

(56) References Cited

U.S. PATENT DOCUMENTS

| 4,041,031 A | 8/1977 | Heasman |
| 5,902,276 A * | 5/1999 | Namey, Jr. .......... A61M 5/31511 604/218 |

(Continued)

FOREIGN PATENT DOCUMENTS

| DE | 200 10 478 U1 | 10/2000 |
| DE | 20 2008 007 834 U1 | 9/2008 |

(Continued)

OTHER PUBLICATIONS

International Search Report dated May 16, 2019 in corresponding International Patent Application No. PCT/EP2018/084963, filed Dec. 14, 2018.

*Primary Examiner* — Edmund H Lee
(74) *Attorney, Agent, or Firm* — Global IP Counselors, LLP

(57) ABSTRACT

A method of making a two-component piston, the two-component piston including a piston cover as the first component and a piston body as the second component. The piston cover is arranged adjacent to the piston body and is configured to be moved relative to the piston body.

17 Claims, 5 Drawing Sheets

(51) Int. Cl.
  *B29C 45/00* (2006.01)
  *B65D 81/32* (2006.01)
  *B65D 83/00* (2006.01)
  B29K 23/00 (2006.01)
  B29K 67/00 (2006.01)
  B29K 77/00 (2006.01)
  B29L 31/00 (2006.01)

(52) U.S. Cl.
  CPC ........ B29C 45/1676 (2013.01); B65D 81/325 (2013.01); B65D 83/0005 (2013.01); *B29C 2045/0027* (2013.01); *B29C 2045/1682* (2013.01); *B29K 2023/06* (2013.01); *B29K 2023/065* (2013.01); *B29K 2067/006* (2013.01); *B29K 2077/00* (2013.01); *B29L 2031/7494* (2013.01)

(56) References Cited

U.S. PATENT DOCUMENTS

| | | | | |
|---|---|---|---|---|
| 6,004,300 | A * | 12/1999 | Butcher | B29C 45/1675 604/218 |
| 8,071,001 | B2 * | 12/2011 | Boucherie | A61M 5/31511 264/328.8 |
| 8,091,864 | B2 * | 1/2012 | Smith | F16K 27/0209 251/332 |
| 2006/0089602 | A1 | 4/2006 | Boucherie | |
| 2007/0119868 | A1 | 5/2007 | Kraemer | |
| 2008/0041885 | A1 | 2/2008 | Costa et al. | |
| 2008/0250546 | A1 | 10/2008 | Watabiki | |
| 2010/0147896 | A1 | 6/2010 | Obrist | |
| 2010/0200617 | A1 | 8/2010 | Schaer | |
| 2012/0247323 | A1 | 10/2012 | Obrist | |
| 2012/0258422 | A1 | 10/2012 | Leiner et al. | |
| 2013/0277390 | A1 | 10/2013 | Buck et al. | |
| 2014/0208939 | A1 | 7/2014 | Frey | |

FOREIGN PATENT DOCUMENTS

| | | |
|---|---|---|
| EP | 0375778 A1 | 7/1990 |
| EP | 0783082 A1 | 7/1997 |
| EP | 2198970 A1 | 6/2010 |
| EP | 2998030 A1 | 3/2016 |
| WO | 2005/094714 A1 | 10/2005 |

\* cited by examiner

METHOD OF MAKING A TWO-COMPONENT PISTON

CROSS-REFERENCE TO RELATED APPLICATION

This application is a U.S. National Stage application of International Application No. PCT/EP2018/084963, filed Dec. 14, 2018, which claims priority to European Patent Application No. 17209077.1, filed Dec. 20, 2017, the contents of each of which are hereby incorporated herein by reference.

BACKGROUND

Field of the Invention

The present invention relates to a method of making a two-component piston, the two-component piston comprising a piston cover as the first component and a piston body as the second component, wherein the piston cover is arranged adjacent to the piston body and is configured to be moved relative to the piston body. The invention further relates to an injection mold for a two-component piston, to a two-component piston and to a cartridge.

Background Information

A wide variety of ways of dispensing masses from cartridges is known in the prior art. The masses can be so-called one-component masses, this means single component materials that e.g. harden via a chemical reaction which is brought about either by an external energy source, such as UV light or heat, or e.g. due to moisture etc. present in the surroundings of the position of application. Typical applications of one component materials can be found e.g. in the dental field or in the building industry, for example to bond products such as windows and concrete elements, or to provide seals between different components.

Another known type of mass is a multi-component mass. The materials to be dispensed are typically a matrix material and a hardener. The filled cartridges come in different ratios referred to as 1:1, 2:1, 4:1 and 10:1 etc., the numbers specifying the ratios of the amounts of each of the two materials that are to be dispensed. The reason for these different ratios is to allow a wide variety of different compositions to be mixed and dispensed. For example, some compositions require more hardener and some require less hardener. Also some compositions require more mixing. Mixing tips are known from the prior art which are adapted to mix the compositions as they exit the cartridge.

Two-component materials are typically used in the dental field as impression materials, e.g. on the formation of dental impressions, as a cement material for prosthetic restorations, as a temporary cement for trial cementing restorations or for cementing temporary crowns. Further applications of two-component materials are present in the building industry where they are e.g. used as a replacement for mechanical joints that corrode over time. Adhesive bonding can be used to bond products such as windows and concrete elements. The use of multi-component materials as protective coatings, for example, in the form of moisture barriers, corrosion protection and anti-slip coatings, is also becoming increasingly common. Examples of flowable materials which can be used are, for example, distributed by the company Coltene using the tradename AFFINIS® or by the company DMG using the tradename PermaCem. One-component and multi-component materials are frequently very expensive and thus it is desired to increase the storage life of these materials, particularly if the cartridges and the materials are designed not just for a single use, but such that they can be used a multiple amount of times over considerable periods of time of e.g. days, weeks or even months.

SUMMARY

In order to increase the storage time of the components, the cartridges to be filled have to be made from materials which do not react with the masses stored therein. Moreover, the cartridges have to be clean, i.e. they should not include any water residue etc., in particular in connection with the storage of single component masses. On filling the cartridges, the cartridges are typically filled either via their outlet with the piston already being positioned in the cartridge or the cartridge is filled from the end where the piston is normally received before the installation of the piston. In both cases air can be trapped between the piston and the material to be stored therein. This air can lead to a reaction of the materials present in the cartridge and hence reduce the storage life of the materials present in the cartridge.

Moreover, during the manufacture of two-component pistons comprising a piston cover separate from a piston body, problems are sometimes encountered in use of the pistons.

Some of these problems arise due to an insufficient attachment of the piston cover at the piston body, this leads to an insufficient seal being present between the piston cover and the piston body. An insufficient seal can allow air to arrive in the cartridge and hence reduce the life time of the components stored in the cartridge.

Moreover, the pistons are typically formed in an injection molding process. During the molding of the piston cover and/or of the piston body sprue marks remain at the point of injection of the injection molding material. For simplicity of manufacture of the injection mold, these points of injection are present at one side of the piston, namely the side from which the valve is accessible. For piston covers this means that the sprue mark is present in the region of an end of the valve pin, with regard to the piston body this sprue mark is present in the region of attachment of a plunger used to drive the piston in a cartridge. These sprue marks can naturally vary in size and depending on their size and orientation can interfere with the operation of the valve pin (i.e. pressing the pin on the rear side of the piston cover).

If the valve pin is not operated correctly, then residual air present in the cartridge in the region of the piston cover after filling cannot be vented correctly from the filled cartridge. This residual air can also reduce the life time of the components stored in the cartridge.

In view of the foregoing it is an object of the invention to provide an improved method of making a piston, with the resultant piston facilitating an improved storage lifetime of materials stored in a filled cartridge. It is a further object of the present invention to provide an improved method of making a piston, with the resultant piston being improved in use in comparison to the prior art.

This object is satisfied by a method as described herein.

Such a method of making a two-component piston, in which the two-component piston comprises a piston cover as the first component and a piston body as the second component, wherein the piston cover is arranged adjacent to the piston body and is configured to be moved relative to the piston body, comprises the steps of:

forming the piston cover, and subsequently
forming the piston body at the piston cover.

By forming the piston cover first, the piston cover can e.g. be used as a mold for the piston body, thereby ensuring an improved attachment of the piston cover at the piston body. Since the piston body is, preferably directly, formed at the piston cover problems associated with the attachment of the piston cover to the piston body can be avoided.

Preferably the piston body is non-releasably formed at the piston cover. By forming the piston body in a non-releasable manner at the piston cover, the attachment of the piston cover to the piston body is improved and the problems associated with the attachment of the piston cover at the piston body can be avoided.

In this way a piston is made available by which the storage lifetime of the components stored in the cartridge can be further improved.

The piston cover comprises an aperture, with the piston body comprising a web that is formed while forming the piston body at the piston cover such that the web of material of the piston body extends through the aperture. In this way a reliable attachment of the piston cover at the piston body is ensured on forming the piston body.

Advantageously the piston cover has a front side and a rear side, with the rear side being arranged adjacent to the piston body, wherein the piston cover is formed starting from a position present at the front side of the piston cover, preferably wherein the piston cover has a central region and wherein the piston cover is formed starting from a position present at the central region.

Forming the piston cover starting at the front side of the piston, means a piston cover having a sprue mark at the front side of the piston cover results. Consequently such a piston does not comprise a sprue mark at the valve pin that could interfere with the venting action. A piston having a sprue mark at the front side can be vented more effectively than prior art pistons.

It is preferred if the piston body has a front end and a rear end and a wall peripherally extending around the piston body between the front end and the rear end, wherein the piston body is formed starting from a position present at the wall, preferably wherein the wall has a recess and the piston body is formed starting from a position present at the recess.

Thus, in the method of manufacturing the two-component piston, the sprue marks for the piston cover and for the piston body are moved in comparison to prior art molds. In the prior art processes, the plastic was injected from the bottom of the pin which is also the position where the valve is operated (by pressing the pin in the direction of the material side). In order to minimize the size of the sprue mark formed there good care needed to be taken to keep the sprue mark under control. This necessitated the use of a needle valve for the hot runner which is rather expensive, the use of such a needle valve can be avoided in the present method of making a two-component piston.

Preferably the piston body is non-releasably formed at the piston cover by a non-releasable connection present between the piston body and the piston cover, wherein the non-releasable connection is produced by a part of the piston body that is formed to extend through an attachment portion of the piston cover. By forming a part of the piston body such that it projects through an attachment portion of the piston cover an improved connection between the piston cover and the piston body is achieved that ensures a correct attachment of the piston cover at the piston body.

Due to the design of the non-releasable connection, the attachment of the piston cover to the piston body is improved and the problems associated with the attachment of the piston cover at the piston body can be avoided.

In this way a piston is made available by which the storage lifetime of the components stored in the cartridge can be further improved.

Advantageously the attachment portion is at least partly, preferably completely, received in the piston body after the step of forming the piston body has been completed. Forming the attachment portion such that it is received in the piston body means it does not interfere with the front side of the piston cover in use of the piston.

It is preferred if the part of the piston body that extends through the attachment portion is formed by a web of material that extends through the attachment portion, preferably through an aperture of the attachment portion, with the web of material being non-releasably connected to two sections of the piston body. This type of design ensures a compact realisation of the non-releasable connection that is simple to manufacture and effective in use. Moreover, the use of an aperture enables a part of the piston body to extend through the piston cover and hence facilitates the attachment of the piston cover to the piston body.

Preferably at least one of the piston cover and the piston body are formed in an injection molding process. Injection molding processes are cost effective and suitable for the mass production of small parts.

A two-component piston is advantageously used since this, on the one hand, enables venting of air present at the first side of the piston between the first side and a material stored in a filled cartridge.

Advantageously the piston body and the piston cover are formed from different materials, so that the piston body and the piston cover can be tailored to the specific uses of each component. For example, the piston cover can be made from a material which is harder than that of the piston body, and which is also less likely to react with the components stored in the cartridge. This can extend the life time of the piston and hence the storage life of components stored in the piston. At the same time the piston body that e.g. comprises the sealing lip can be made from a soft material, such as PE (polyethylene), that reliably ensures a seal between the piston and a cartridge wall due to the materials used.

It is preferred if the piston cover and the piston body are formed in an injection mold by the injection molding process, the method comprising the steps of:
 forming the piston cover in a first mold;
 optionally removing parts of the first mold specific to a rear side of the piston cover from the injection mold after at least partly, preferably completely curing the piston cavity; and
 using the piston cover as a part of a second mold for the piston body. These are advantageous steps that can be carried out to form the piston cover and the respective piston in a cost-effective, facile and quick manner.

Advantageously the method further comprises the steps of:
 maintaining the piston cover in the injection mold as part of the second mold; or
 introducing the piston cover into the second mold
 optionally introducing further parts of the second mold specific to the piston body;
 optionally arranging the further parts of the second mold specific to the piston body relative to the piston cover;
 forming the piston body in the second mold;
 at least partly, preferably completely, curing the piston body in the second mold; and removing the two-component piston from the second mold. These are advantageous steps that can be carried out to form the piston body at the piston cover and hence the piston in a cost-effective, facile and quick manner.

It is preferred if a first point of injection for injection molding material for the piston cover is present at a part of the first mold configured to mold a front side of the piston cover. Injecting the injection molding material at a front side of the piston cover rather than at the rear side of the piston cover means that no sprue mark is formed at the rear side.

Advantageously the piston cover is formed to have a central region at the front side and the first point of injection is present at a part of the first mold configured to mold a crown, i.e. a center, of the central region. By injection molding the piston cover from an, in particular geometric, center of the piston cover ensures a uniform formation of the piston cover, as the injection molding material can spread from this center in a homogenous manner ensuring the formation of high quality piston covers.

Preferably the piston body is formed to have an outer lateral wall extending from a first side of the piston to a second side of the piston, with the second mold comprising a second point of injection for injection molding material for the piston body present in a region of a part of the second mold configured for the outer lateral wall of the piston body, preferably wherein the outer lateral wall of the piston body comprises a recess, with the second point of injection being present in the vicinity of the part of the second mold configured for the recess. In this way the sprue mark of the piston body is altered from that of prior art pistons and is no longer present in the region of the second side of the piston body that is configured to interact with a plunger for dispensing materials from a cartridge.

In a further aspect the present invention relates to an injection mold for a two-component piston, the two-component piston comprising a piston cover as the first component and a piston body as the second component, wherein the piston cover is arranged adjacent to the piston body, the injection mold comprising a first mold for the piston cover, the first mold having a first injection channel forming a first point of injection for the injection molding material for the piston cover, the first point of injection being present at a part of the first mold for molding a front side of the piston cover, the injection mold further comprising a second mold for the piston body, with the piston cover forming a part of the second mold.

In prior art molds, the plastic is injected from the bottom of the valve pin which is also the position where the valve is operated (by pressing the valve pin in the direction of the material side). In order to minimize the size of the sprue mark formed there good care needed to be taken to keep the sprue mark under control. This necessitated the use of a needle valve for the hot runner which is rather expensive. Thus, the injection mold in accordance with the present invention can be produced in a more cost effective manner, as no needle valve is required. Moreover, the fact that less care is required to keep the sprue mark under control, the number of rejects can be reduced, hence the injection mold can be used for a more economic manufacture of the piston covers respectively of the pistons.

Advantageously the second mold comprises a second point of injection for the injection molding material for the piston body, with the second point of injection being present in a region of a part of the second mold for an outer lateral wall of the piston body.

Thus, in the mold used for manufacturing the two-component piston, the sprue marks for the piston cover and for the piston body are moved in comparison to prior art molds, namely to positions which do not interfere with the operation of the valve of the piston.

In accordance with a further aspect the present invention relates to a two-component piston for a cartridge obtainable by a method in accordance with the teaching presented herein or by an injection mold in accordance with the teaching presented herein, the two-component piston comprising the piston cover as the first component and the piston body as the second component, wherein the piston cover is configured to be moved relative to the piston body and wherein the piston cover is non-releasably connected to the piston body, with the non-releasable connection between the piston body and the piston cover being produced by a part of the piston body that extends through an attachment portion of the piston cover.

By forming a part of the piston body such that it projects through an attachment portion of the piston cover an improved connection between the piston cover and the piston body is achieved that ensures a correct attachment of the piston cover at the piston body.

Due to the design of the non-releasable connection, the attachment of the piston cover to the piston body is improved and the problems associated with the attachment of the piston cover at the piston body can be avoided.

In this way a piston is made available by which the storage lifetime of the components stored in the cartridge can be further improved.

A two-component piston is advantageously used since this enables a venting of air present at the first side of the piston between the first side and a material stored in a filled cartridge.

In accordance with a further aspect the present invention relates to a cartridge comprising an outlet, at least one chamber and at least one piston in accordance with the teaching presented herein, with one piston being arranged in each of the at least one chambers, the cartridge preferably further comprising a respective flowable mass arranged in each of the at least one chambers.

By using a piston as discussed herein in a cartridge means that the cartridge can be vented in an improved manner ensuring that one can remove air present in the chamber of a cartridge between the component present in the chamber and the piston to obtain a longer storage life time of the component present in that chamber.

It is preferred if a cartridge comprises a respective flowable mass arranged in each of the at least one chambers. Typical dispensing systems have volumes for the flowable masses selected from the range of volumes comprising 2.5 ml, 5 ml, 10 ml, 20 ml, 50 ml and 100 ml, 500 ml and 2500 ml with the volume being a combined volume for both chambers of the cartridge. Thus, in a preferred embodiment the dispensing system has a volume in the range of 1 to 2500 ml, more preferably of 1 to 500 ml.

BRIEF DESCRIPTION OF THE DRAWINGS

The invention will be explained in more detail hereinafter with reference to the drawings.

DETAILED DESCRIPTION OF THE EMBODIMENTS

Figure 1:
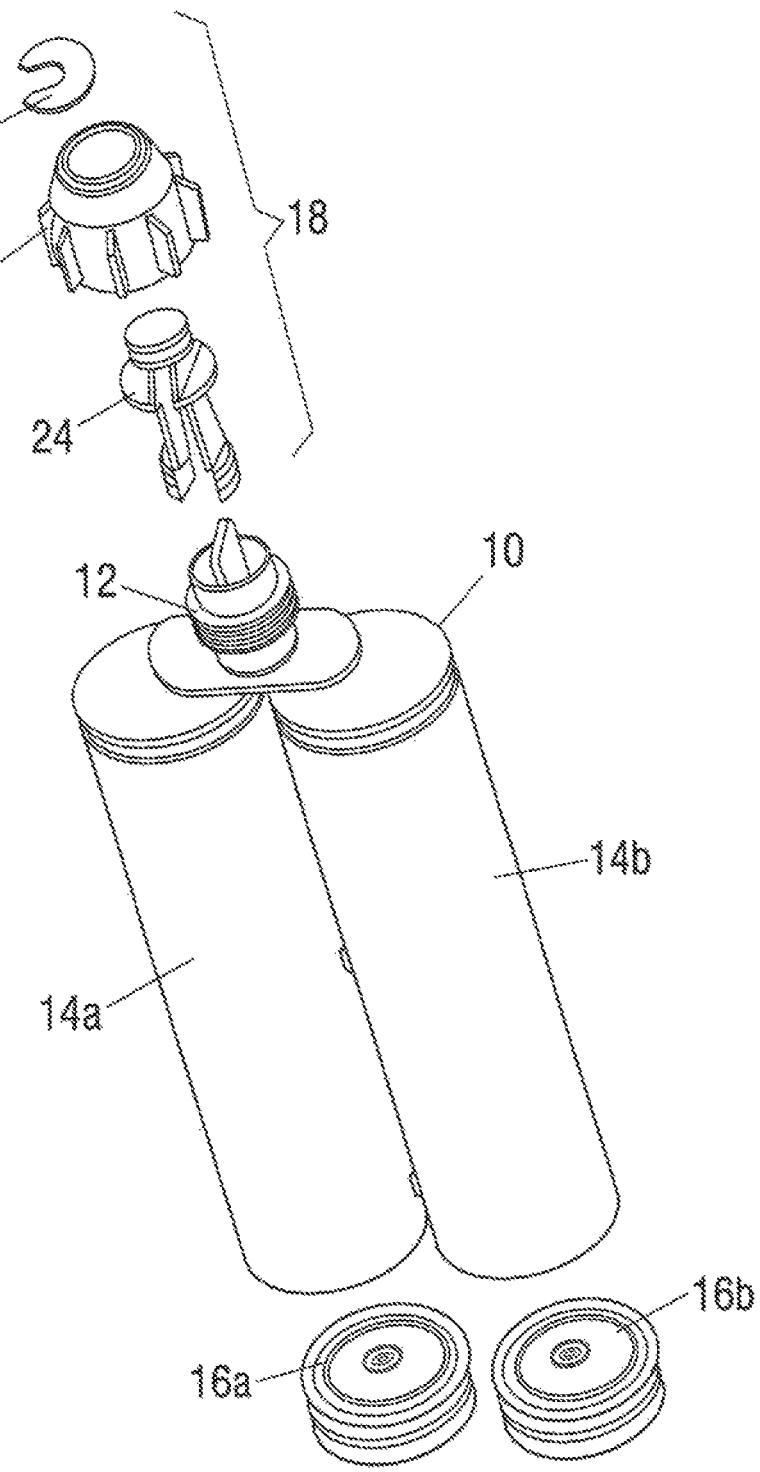
FIG. 1 is an exploded view of components of an embodiment of a cartridge.

Features which have the same or a similar function will be described in the following using the same reference numeral. It is also understood that the description given with respect to reference numerals used in one embodiment also applies to the same reference numerals in connection with other embodiments unless something is stated to the contrary.

FIG. 1 shows a first embodiment of a cartridge 10. The cartridge 10 comprises an outlet 12, two chambers 14a, 14b and two pistons 16a, 16b. The outlet 12 of the cartridge 10 is sealed through the use of a cap mechanism 18. The cap mechanism 18 comprises a cap 20 which is secured to the cartridge 10 by a circlip 22 engaging a sealing plug 24. The outlets 12 are sealed through the use of the sealing plug 24. The cartridge 10 shown in FIG. 1 is a so-called 1:1 cartridge 10.

Figure 2:
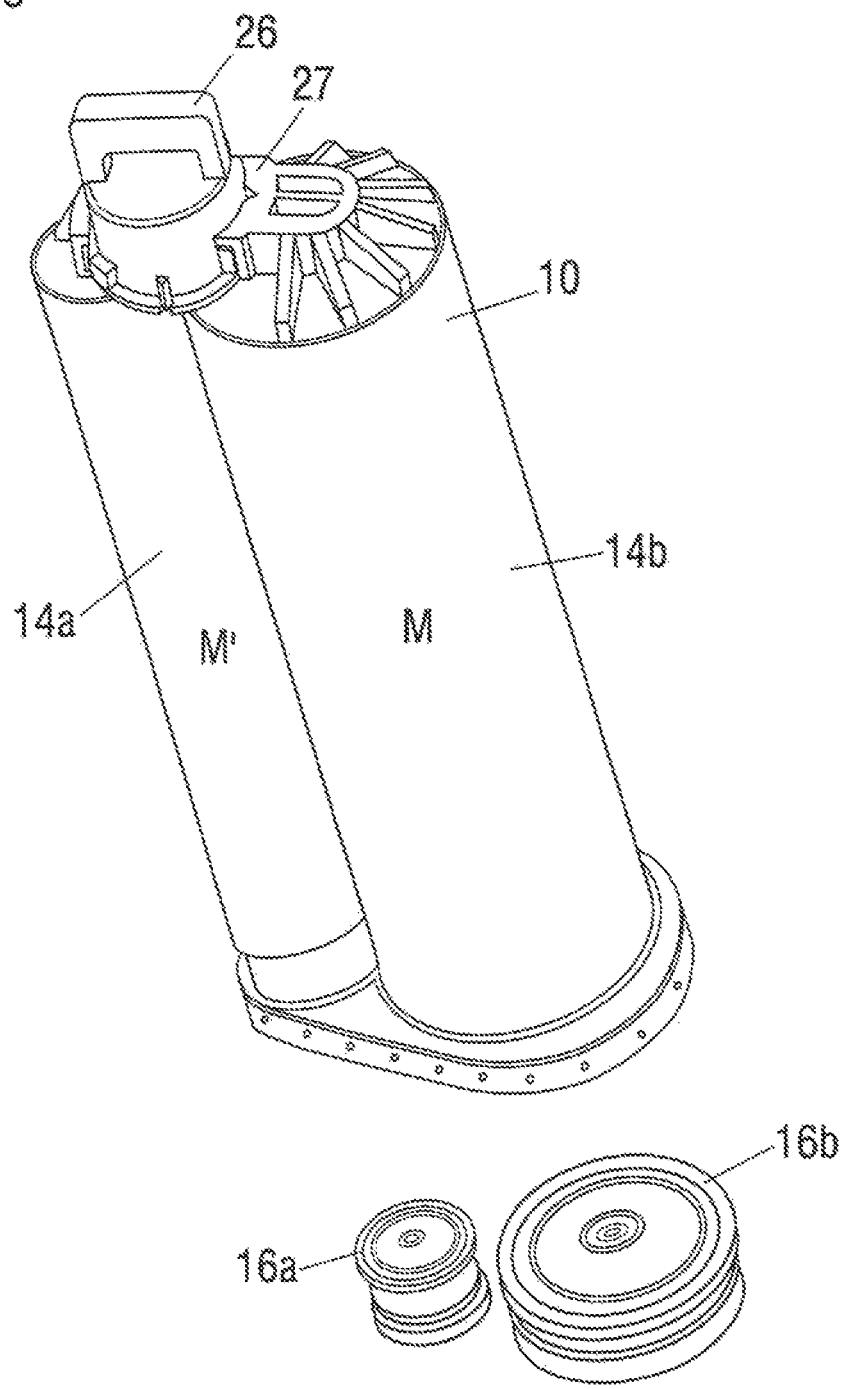
FIG. 2 is a further exploded view of components of a further embodiment of a cartridge.

FIG. 2 shows a further embodiment of a cartridge 10. In contrast to the embodiment of FIG. 1 the cartridge 10 of FIG. 2 shows a so-called 4:1 cartridge 10. This means that a volume of material M that can be stored in the first chamber 14b is four times a volume of material M' that can be stored in the second chamber 14a. A further difference between the cartridges 10 of FIG. 1 and FIG. 2 is the closure cap 26. The closure cap 26 of FIG. 2 is secured at the cartridge 10 by a so-called bayonet means or device 27 as is well known in the art. Other kinds of closure caps (not shown) can also be used to seal off the outlet 12 from the cartridge 10.

The closure cap 26, the cap mechanism 18 and the ratios of cartridges 10 shown in FIG. 1 and FIG. 2 can be arbitrarily combined, depending on the specific use of the cartridge 10 and/or of the materials to be dispensed using said cartridge 10. Since the volume of the chambers 14a, 14b of the cartridge of FIG. 2 is different, the outer diameter, i.e. the size of the pistons 16a, 16b employed in the chambers 14a, 14b is also different as is clear from FIG. 2.

Figure 3:
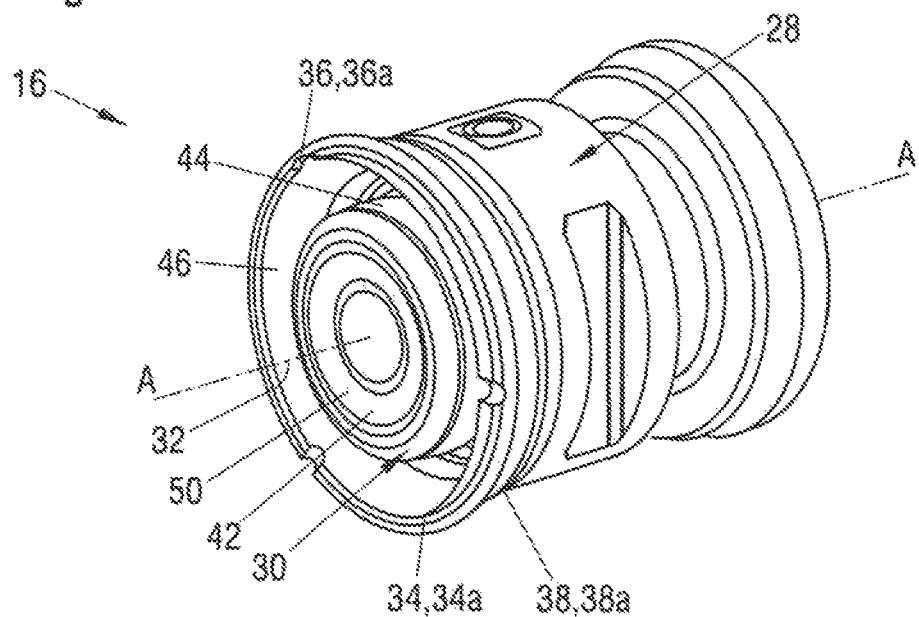
FIG. 3 is a view of an embodiment of a piston.

FIG. 3 shows a schematic view of a piston 16. The piston 16 comprises a generally cylindrically shaped piston body 28 and a piston cover 30. The piston cover 30 covers at least a substantial part of a first side 32 of the piston 16. The piston body 28 further comprises a centering portion 34 in the form of a circumferentially extending chamfered lip 34a at the first side 32. The lip 34a has three venting slots 36 disposed therein as venting means or system 36a in order to permit venting of air present between the lip 34a and a chamber wall of the cartridge (not shown) once the piston 16 is installed in the cartridge 10 and the venting process is carried out.

A sealing lip 38 is disposed beneath the chamfered lip 34a as a sealing means or device 38a. The selling lip 38 is provided to ensure a seal between the cartridge 10 and the piston 16 in order to prevent air or the like from entering or exiting the cartridge 10 via the sealing lip 38. As can be seen the sealing lip 38 is adjacent to the centering portion 34.

Moreover, a boundary of the venting slots 36 is preferably directly adjacent to a boundary of the sealing lip 38 which is adjacent to the centering portion 34. This ensures that the venting means 36a are positioned such that air can be reliably vented from the space between the centering lip 34 and the cartridge wall. In the Figure shown, the venting slots 36 have the form of a generally U-shaped valley in a cross-section thereof. Naturally speaking any other kind of shape can be selected for the venting slots 36, such as a V-shaped valley or a simple through bore extending through the centering portion.

On insertion of the piston 16 into the cartridge 10 the centering portion 34 not only functions as a centering aid to protect the sealing lip 38 from becoming damaged on insertion of the piston 16 into the cartridge and thus aids in avoiding leaks, but also as a scraper and thereby helps to clear material and any particles present at the cartridge wall from the area close to the cartridge wall (this is naturally only the case when the materials include particles).

In this connection it should be noted that the piston cover 30 is typically made from a material different from that of the piston body 28. The material of the piston cover 30 can e.g. comprise PE or PBT; that of the piston body 28 can e.g. comprise PA (polyamide) or HDPE. In a preferred embodiment of the two-component piston 16, the piston cover 30 comprises PBT and the piston body 28 comprises HDPE.

The piston cover 30 has a concavely shaped central region 42 which can be considered to have the shape of a plate. Venting grooves (not shown) can be disposed at a front side 50 of the piston cover 30 to facilitate the air removal from the concavely shaped central region 42. Such venting grooves could extend from the central region 42 of the piston cover 30, and also project downwardly along a peripherally extending side portion 44 of the piston cover 30 into a groove 46 formed within the piston body 28. The venting grooves could extend into the groove 46 over a complete height of the side portion 44.

Figure 4:
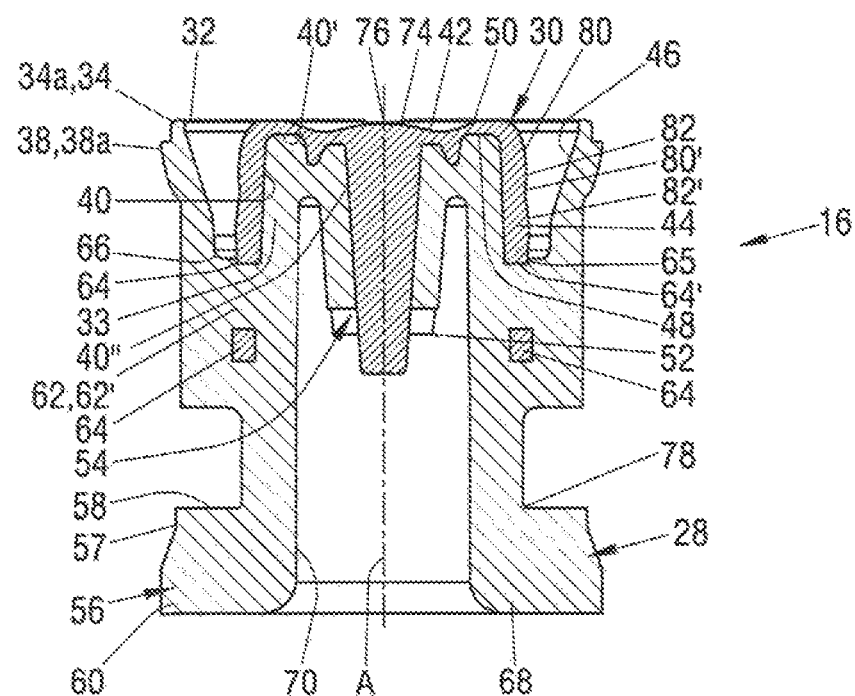
FIG. 4 a section through the piston of FIG. 3.

FIG. 4 shows a section through the piston 16 of FIG. 3 along the sectional line A-A of FIG. 3 that coincides with a longitudinal axis A of the piston 16. The piston cover 30 extends into the peripherally extending groove 46 of the piston body 28. Moreover, the piston cover 30 has the front side 50 at the first side 32 and a rear side 48. The rear side 48 has a shape which is complementary to a substantial part of the shape of the first side 32 of the piston body 28. The piston cover 30 also has a so-called valve pin 52 which forms part of a valve 54 arranged between the piston cover 30 and the piston body 28. The center of the valve pin 52 coincides with the longitudinal axis A of the piston 16. At the first side 32, the piston body 28 comprises an inner wall 33 having a top end 40', an outer surface 40 and a valve surface 40". Parts of the rear side 48 the piston cover 30 are supported at the inner wall 33 in a non-venting state of the piston 16.

On installation of the piston 16 into the cartridge 10, the valve pin 52 can be actuated. Thereby the piston cover 30 is lifted off from the piston body 28 and permits an air flow in a venting channel (not shown) then present between the rear side 50 of the piston cover 30 and the wall 33 of the piston body 28, i.e. between the piston cover and the top end 40', the outer surface 40 and the valve surface 40". This then permits a venting of residual are present at the first side 32 of the piston 16 from the front side 50 of the piston cover via the valve 54.

On actuating the valve pin 52 from the second side 68, the valve pin 52 is moved along the longitudinal axis A in the direction of the piston cover 30 causing the concavely shaped central region 42 to deflect and to become less concave or in some instances even convex. Thereby forming the venting channel (not shown) between the rear side 50 of the piston cover 30 and the piston body 28 in the region of the top end 40', the outer surface 40 as well as the valve surface 40".

The longer a length of the valve pin 52 selected, the further the piston cover 30 can be lifted from the piston body 28. Thereby, a space of the venting channel provided for air to be vented from the cartridge 10 via the piston 16 is enlarged. Rather than using the valve pin 52 shown in the Figures other forms of valve members 52a, such as a hollow cylindrical member (not shown) can be used. The valve member 52a has two functions, namely to cooperate with a plunger for venting and with the valve surface 40" of the piston body to form the valve 54.

The piston 16 has an outer peripheral surface 56 formed by a peripherally extending outer wall 57, with the annular groove 46 being formed between the outer wall 57 and the inner wall 33.

The outer peripheral surface 56 respectively the outer wall 57 of FIG. 4 has a substantially cylindrical outer shape and has the chamfered centering lip 34 at the first side 32. Following an outer contour of the outer peripheral surface 56 from the first side 32 to a second side 68 of the piston 16, the piston body 28 comprises the centering lip 34, the sealing lip 38, a first recess 58 and a stabilizing projection 60 formed at the second side 68. The first recess 58 is arranged between the sealing lip 38 and the stabilizing projection 60.

The stabilizing projection 60 is disposed on the piston 16 in order to stabilize the piston 16 as it travels along the cartridge wall during a dispensing action. This ensures that the piston 16 travels along the cartridge wall in an as uniform as possible manner.

Moreover, a sprue mark 78 is present in the first recess 58, indicating that the piston body 28 is formed in an injection molding process and that the point of injection of the molding material at the corresponding mold 96 (see FIG. 6B) is present in a region of the mold designed to form the outer wall 57.

The second side 68 of the piston 16 further comprises a central recess 70 into which a plunger (not shown) can be introduced in order to actuate the valve pin 52. The second side 68 can further be actuated to move the piston 16 in the cartridge to dispense a material M, M' present in the cartridge 10 via the outlet 12.

The plunger is designed such that it does not engage the valve 54 during a dispensing action, as otherwise a component present in the cartridge 10 could leak out of the cartridge 10 via the central recess 70 on dispensing.

The piston body 28 can comprise an O-ring (not shown) arranged at the outer peripheral surface 56. Such sealing O-rings are advantageously used, in order to ensure a continuous seal of cartridges that are not only used for one application, but for many applications spaced apart in time.

The piston cover 30 is non-releasably connected to the piston body 28. The non-releasable connection is formed by a part 62 of the piston body 28 extending through an attachment portion 64 of the piston cover 30. The piston cover 30 comprises at least two attachment portions 64 for the non-releasable connection between the piston cover 30 and the piston body 28. The piston body 28 comprises two parts 62 that each respectively extend through a respective attachment portion 64. The attachment portions 64 are arranged such that they face one another on opposite sides of the longitudinal axis A. The attachment portion 64 projects from the piston cover 30 at least generally in the direction of the second side 68.

Each attachment portion 64 comprises an aperture 64' (see also FIGS. 5A to 5C) and the part 62 of the piston body 28 that extends through the attachment portion 64 at least substantially completely fills an internal space of the aperture 64'.

In the present example the part 62 of the piston body 28 that extends through the attachment portion 64 is formed by a web 62' of material that extends through the attachment portion 64. The web of material is non-releasably connected to two sections of the piston body 28 disposed on either side of the attachment portion 64. The web 62' is formed from the same material as the piston body. Similarly the attachment portion 64 is formed from the same material as the piston cover 30.

The attachment portion 64 is integrally formed with the piston cover and projects from the piston cover 30 at a region of a base 66 of the groove 46 of the piston body 28 in the direction of the second side 68. The attachment portion 64 is completely received in the piston body. To this end the base 66 of the groove 46 comprises an attachment portion recess 65. The piston body 28 is formed around the attachment portion 64 and adjacent to the piston cover 30.

The central region 42 of the piston cover comprises a crown 74. A sprue mark 76 is present at the center of the crown 74. This sprue mark 76 indicates that the piston cover 30 was injection molded and that the point of injection of the molding material at a corresponding mold 92 (see FIG. 6A) is present in the region of the crown 74.

Figure 5A:
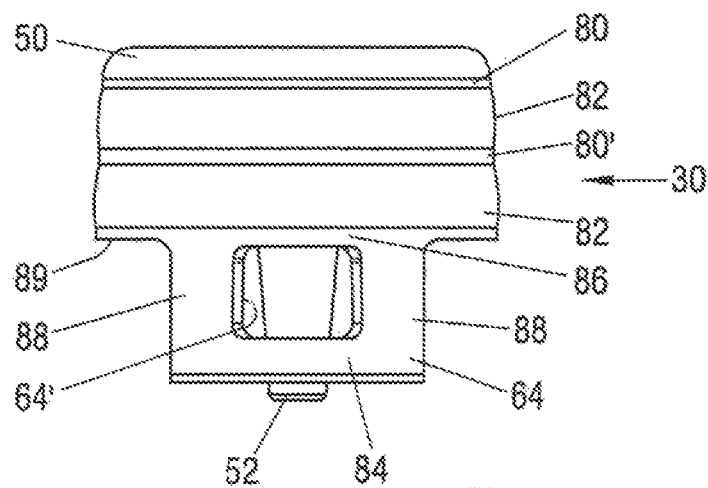
FIG. 5A is a first side view of a piston cover.
Figure 5B:
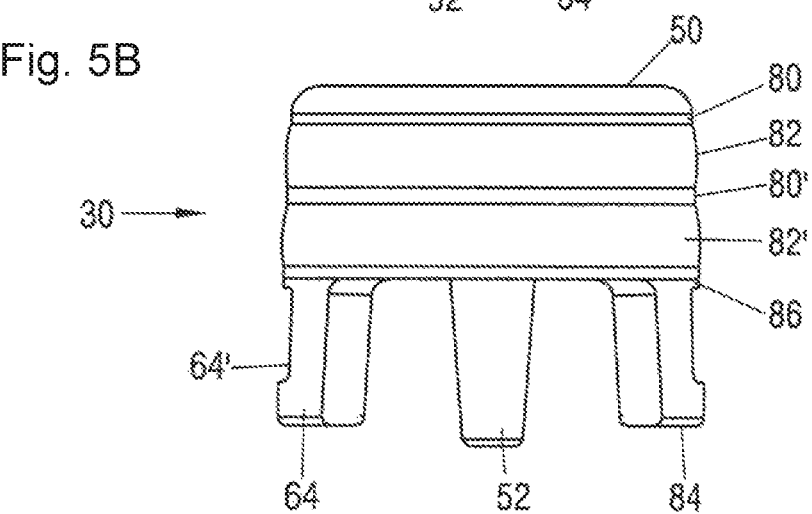
FIG. 5B is a second side view of the piston cover of FIG. 5A.
Figure 5C:
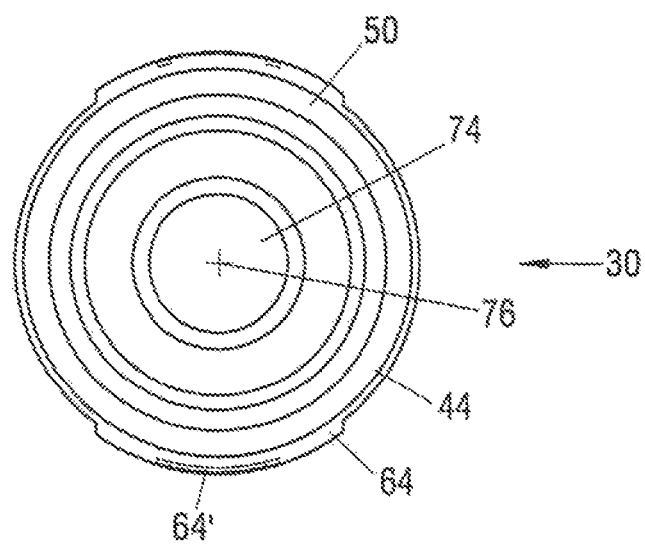
FIG. 5C is a view from above of the piston cover of FIG. 5A.

FIGS. 5A to 5C show various views of the piston cover 30. As can be seen the aperture 64' has an at least generally rectangular shape. The dimensions of the aperture 64' are chosen such that the lower frame 84 of the aperture 64' (i.e. the part which is completely embedded in the second plastic) is located roughly at equal distances to the surrounding exterior surfaces of the piston body 28, i.e. the outer wall 57 and a wall of the recess 70. The lower frame 84 is connected to the upper frame 86 of the attachment portion 64 via two arms 88. In the drawing shown a width of the arms 88 is greater than a height of the lower frame 84. The height of the lower frame could also be more than a width of the arms 88 or equivalent thereto. The upper frame 86 is integrally formed at a lower side 89 of the piston cover 30 and thus projects from the piston cover 30 at the lower side 89 thereof.

The side portion 44 of the piston cover has an undulated shape indicated by two recesses 80, 80' and two peaks 82, 82'. These features are present in order to ensure a gripping of the piston cover 30 during a forming of the piston body 28 as will be discussed in the following.

Figure 6A:
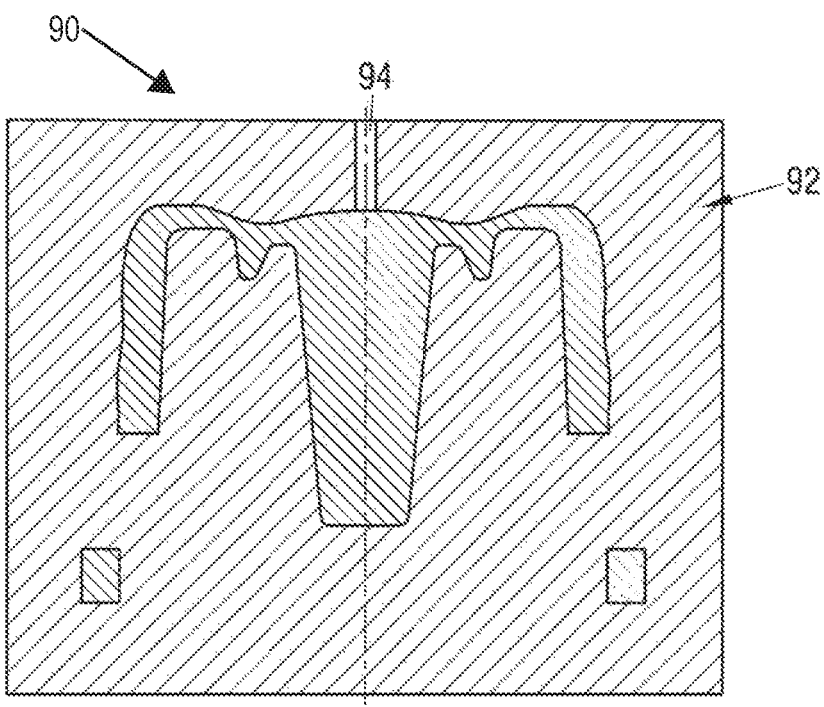
FIG. 6A a schematic section through a first mold of an injection molding tool.

FIG. 6A shows a schematic section of an injection mold 90 for the two-component piston 16 discussed in the foregoing. The injection mold 90 comprises a first mold 92 for the piston cover 30. The first mold has a first injection channel 94 forming a first point of injection for the injection molding material for the piston cover 30. The first injection channel 94 is present at a part of the first mold 92 for molding the front side 50 of the piston cover 30.

The injection molding material is introduced into the first mold 92 at the respective temperatures and pressures typically used for the material of the piston cover 30 via the first injection channel 94. On molding the piston cover 30 the sprue mark 76 will be present at the crown 74.

Figure 6B:
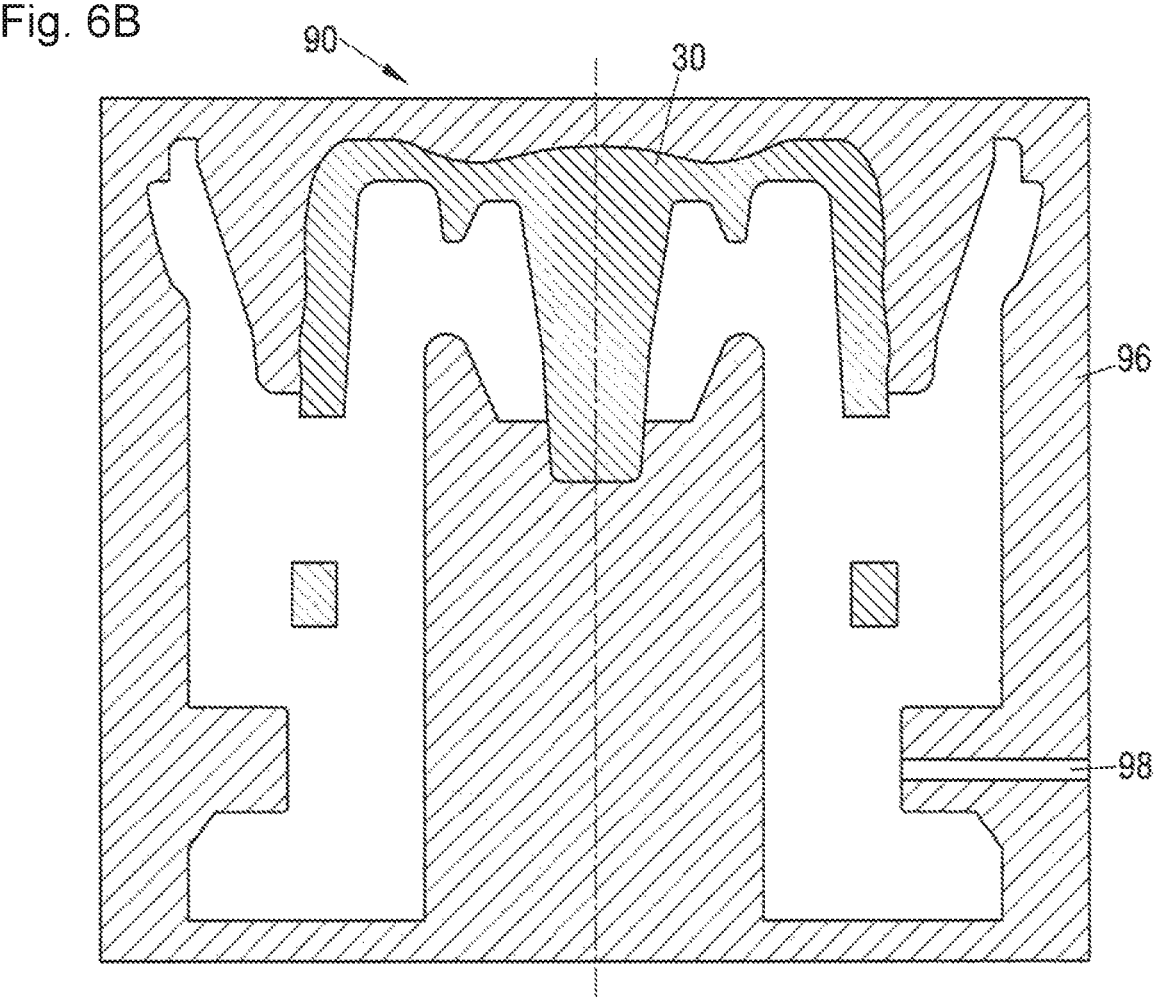
FIG. 6B a schematic section through a second mold of the injection molding tool.

As shown in FIG. 6B, the injection mold 90 further comprises a second mold 96 for the piston body 28. On injection molding the piston 16, the piston cover is initially molded in the first mold 92 and subsequently forms a part of the second mold 96.

The second mold 96 comprises a second injection channel 98 forming a second point of injection used for the injection of molding material for the piston body 28. The second point of injection is present in a region of a part of the second mold 96 for an outer peripheral wall 57 of the piston body 28.

Thus, in the method of manufacturing the two-component piston, the sprue marks for the piston cover 30 and for the piston body 28 are moved in comparison to prior art molds. In the prior art processes, the plastic was injected from the bottom of the pin which is also the position where the valve is operated (by pressing the pin in the direction of the material side). In order to minimize the size of the sprue mark formed there good care needed to be taken to keep the sprue mark under control. This necessitated the use of a needle valve for the hot runner which is rather expensive.

Moving the sprue mark to the front side of the piston cover in the new method, the position of the sprue mark is less critical with respect to any local residual resin. Thus a cheaper runner system can be used. In this connection it should be noted that the position of the sprue needs to be close to the axis of symmetry for the formation of the piston cover 30.

Also the sprue mark 78 for the piston body has been moved from the second side 68 to the outer wall 57 in comparison to prior art molds. This also simplifies the method of manufacture of the piston body 28.

On making a piston the following method of making the two-component piston 16 is carried out: In a first step the piston cover 30 is formed by injecting injection molding material via the first injection channel 94 into the first mold 92. Subsequently in a second step the piston body 28 is formed at the piston cover 30 in the second mold 96.

During the first step the piston cover 30 is formed starting from a position present at the front side 50 of the piston cover 30, more specifically at a position representing the center of the crown 74 of the central region 42. This starting position is later defined by the sprue mark 76 present at the piston cover 30. Once the piston cover 30 has been allowed to cure for a certain period of time either completely or partially, parts of the first mold 92 specific to the rear side 48 of the piston cover 30 are removed from the injection mold 90.

The piston cover 30 is then used as a part of a second mold 96 for the piston body 28. This can be conducted in a further injection mold 90 or in the same injection mold 90 in which the piston cover 30 was formed.

During the second step the piston body 28 is formed starting from a position present at the outer wall 57, more specifically, at a position present at the recess 58 of the outer wall 57 via the second injection channel 98. This second injection channel 98 forms the second point of injection that causes the sprue mark 78 to be formed in the recess 58.

Once the position of the piston cover 30 has been ensured in the second mold 96 the remaining parts of the second mold 96 specific to the piston body 28 are introduced into the injection mold 90. Thereafter, the piston body 28 is formed by introducing injection molding material into the second mold 96 at the respective temperatures and pressures typically used for the material of the piston body 28 via the second point of injection 96. Thereafter, the piston body is allowed to at least partly, preferably completely, cure in the second mold 96, before the final two-component piston 16 is removed from the second mold 96 and made available for assembly with the cartridge 10.

The invention claimed is:

1. A method of making a two-component piston, the two-component piston comprising a piston cover as a first component and a piston body as a second component, the piston cover arranged adjacent to the piston body and configured to be moved relative to the piston body, the method comprising:
   forming the piston cover; and subsequently
   forming the piston body at the piston cover such that the piston body is non-releasably formed at the piston cover by a non-releasable connection present between the piston body and the piston cover, and the non-releasable connection is produced by a part of the piston body that is formed to extend through an attachment portion of the piston cover.

2. The method in accordance with claim 1, wherein the piston cover comprises an aperture, and the piston body comprises a web of material formed while forming the piston body at the piston cover such that the web of material of the piston body extends through the aperture.

3. The method in accordance with claim 1, wherein the piston cover has a front side and a rear side, the rear side being arranged adjacent to the piston body, and the piston cover is formed starting from a position present at the front side of the piston cover.

4. The method in accordance with claim 3, wherein the piston cover has a central region and the piston cover is formed starting from a position present at the central region.

5. The method in accordance with claim 1, wherein the piston body has a first side, a second side and a wall peripherally extending around the piston body between the first side and the second side, and the piston body is formed starting from a position present at the wall.

6. The method in accordance with claim 5, wherein the wall has a recess and the piston body is formed starting from a position present at the recess.

7. The method in accordance with claim 1, wherein the attachment portion is at least partly received in the piston body after the forming the piston body has been completed.

8. The method in accordance with claim 1, wherein the part of the piston body that extends through the attachment portion is formed by a web of material that extends through the attachment portion.

9. The method in accordance with claim 8, wherein the web of material extends through an aperture of the attachment portion, with the web of material being non-releasably connected to two sections of the piston body.

10. The method in accordance with claim 1, wherein the piston cover and the piston body are formed in an injection molding process.

11. The method in accordance with claim 1, wherein the piston body and the piston cover are formed from different materials.

12. The method in accordance with claim 10, wherein the piston cover and the piston body are formed in an injection mold by the injection molding process, and
   the forming the piston cover includes form the piston cover in a first mold of the injection mold, and further comprising
removing parts of the first mold specific to a rear side of the piston cover from the injection mold after at least partly curing the piston cover; and
   using the piston cover as a part of a second mold for the piston body.

13. The method in accordance with claim 12, the method further comprising:
  maintaining the piston cover in the injection mold as part of the second mold; or
  introducing the piston cover into the second mold;
introducing further parts of the second mold specific to the piston body;
arranging the further parts of the second mold specific to the piston body relative to the piston cover;
  forming the piston body in the second mold;
  at least partly curing the piston body in the second mold; and
  removing the two-component piston from the second mold.

14. The method in accordance with claim 12, wherein a first point of injection for injection molding material for the piston cover is present at a part of the first mold configured to mold a front side of the piston cover.

15. The method in accordance with claim 14, wherein the piston cover is formed to have a central region at the front side and the first point of injection is present at a part of the first mold configured to mold a crown of the central region.

16. The method in accordance with claim 13, wherein the piston body is formed to have an outer wall extending from a first side of the piston to a second side of the piston, the second mold comprising a second point of injection for injection molding material for the piston body present in a region of a part of the second mold configured for the outer wall of the piston body.

17. The method in accordance with claim 16, wherein the outer wall of the piston body comprises a recess, and the second point of injection is present in a vicinity of the part of the second mold, which is configured for the recess.

* * * * *